(12) United States Patent
Kukla et al.

(10) Patent No.: US 11,478,289 B2
(45) Date of Patent: Oct. 25, 2022

(54) COMPRESSION FIXATION SYSTEM

(71) Applicant: Numagenesis, LLC (STATE OF NORTH CAROLINA), Hickory, NC (US)

(72) Inventors: Robert Kukla, Hickory, NC (US); Lawrence Binder, Miami, FL (US)

(73) Assignee: Numagenesis, LLC, Hickory, NC (US)

( * ) Notice: Subject to any disclaimer, the term of this patent is extended or adjusted under 35 U.S.C. 154(b) by 138 days.

(21) Appl. No.: 17/045,225

(22) PCT Filed: May 3, 2019

(86) PCT No.: PCT/US2019/030654
§ 371 (c)(1),
(2) Date: Oct. 5, 2020

(87) PCT Pub. No.: WO2019/213560
PCT Pub. Date: Nov. 7, 2019

(65) Prior Publication Data
US 2021/0161573 A1 Jun. 3, 2021

Related U.S. Application Data

(60) Provisional application No. 62/667,247, filed on May 4, 2018.

(51) Int. Cl.
*A61F 2/46* (2006.01)
*A61B 17/88* (2006.01)
(Continued)

(52) U.S. Cl.
CPC ...... *A61B 17/8861* (2013.01); *A61B 2017/00477* (2013.01); *A61B 2017/00867* (2013.01); *A61B 2017/564* (2013.01); *A61B 2017/681* (2013.01)

(58) Field of Classification Search
CPC combination set(s) only.
See application file for complete search history.

(56) References Cited

U.S. PATENT DOCUMENTS

| 2,485,531 A | 10/1949 | Dzus |
| 5,190,543 A | 3/1993 | Schlapfer |

(Continued)

FOREIGN PATENT DOCUMENTS

| DE | 4103494 C1 | 4/1992 |
| EP | 1491148 | 12/2004 |

(Continued)

OTHER PUBLICATIONS

Cachia, V.V., et al., Mechanical Characteristics of the New Bone-LOK Bi-Cortical Internal Fixation Device, Nov./Dec. 2003, 344-349, vol. 42, No. 6, The Journal of Foot & Ankle Surgery, California.

(Continued)

*Primary Examiner* — Sameh R Boles
(74) *Attorney, Agent, or Firm* — McNees Wallace & Nurick LLC

(57) ABSTRACT

A compression fastener system includes an elongate generally rigid coupling component, a toggle anchor at the distal end of the coupling component that can pivot about 90 degrees between inline and out of line with the coupling component, and a generally cylindrical collet that is engageable with a surface of the coupling component, and having two or more legs that splay upon passage of the coupling component through the collet, at least one leg having a cutting edge along at least a portion of its length that can engage with an adjacent rigid element, such as bone, to fix the rigid coupling component, toggle anchor and collet assembly into compression with the rigid element.

16 Claims, 15 Drawing Sheets

(51) Int. Cl.
  *A61B 17/00* (2006.01)
  *A61B 17/56* (2006.01)
  *A61B 17/68* (2006.01)

(56) References Cited

U.S. PATENT DOCUMENTS

| | | | |
|---|---|---|---|
| 5,409,486 | A | 4/1995 | Reese |
| 5,613,968 | A | 3/1997 | Lin |
| 5,797,963 | A | 8/1998 | McDevitt |
| 5,814,071 | A | 9/1998 | McDevitt et al. |
| 5,851,189 | A | 12/1998 | Forber |
| 5,871,504 | A | 2/1999 | Eaton et al. |
| 5,931,840 | A | 8/1999 | Goble et al. |
| 5,944,726 | A | 8/1999 | Blaeser et al. |
| 5,947,967 | A | 9/1999 | Barker |
| 6,162,234 | A | 12/2000 | Freedland et al. |
| 6,206,895 | B1 | 3/2001 | Levinson |
| 6,319,263 | B1 | 11/2001 | Levinson |
| 6,622,731 | B2 | 9/2003 | Daniel et al. |
| 6,673,078 | B1 | 1/2004 | Muncie |
| 6,685,705 | B1 | 2/2004 | Taylor |
| 6,706,045 | B2 | 3/2004 | Lin et al. |
| 6,860,889 | B2 | 3/2005 | Bonati et al. |
| 6,872,209 | B2 | 3/2005 | Morrison |
| 6,887,243 | B2 | 5/2005 | Culbert |
| 6,984,241 | B2 | 1/2006 | Lubbers et al. |
| 6,994,725 | B1 | 2/2006 | Goble |
| 7,083,622 | B2 | 8/2006 | Simonson |
| 7,172,595 | B1 | 2/2007 | Goble |
| 7,270,665 | B2 | 9/2007 | Morrison et al. |
| 7,326,211 | B2 | 2/2008 | Padget et al. |
| 7,485,119 | B2 | 2/2009 | Thelen et al. |
| 7,517,350 | B2 | 4/2009 | Weiner et al. |
| 7,563,275 | B2 | 7/2009 | Falahee et al. |
| 7,578,833 | B2 | 8/2009 | Bray |
| 7,591,838 | B2 | 9/2009 | Kramer et al. |
| 7,641,677 | B2 | 1/2010 | Weiner et al. |
| 7,824,429 | B2 | 11/2010 | Culbert et al. |
| 7,967,820 | B2 | 6/2011 | Bonutti et al. |
| 7,981,143 | B2 | 7/2011 | Doubler et al. |
| 8,080,016 | B2 | 12/2011 | Moorcroft et al. |
| 8,128,627 | B2 | 3/2012 | Justin et al. |
| 8,287,538 | B2 | 10/2012 | Brenzel et al. |
| 8,303,598 | B2 | 11/2012 | Frankel et al. |
| 8,702,768 | B2 | 4/2014 | Tipirneni |
| 8,715,284 | B2 | 5/2014 | Culbert |
| 8,828,067 | B2 | 9/2014 | Tipirneni et al. |
| 2001/0025181 | A1 | 9/2001 | Freedlan |
| 2002/0133148 | A1 | 9/2002 | Daniel et al. |
| 2003/0088270 | A1 | 5/2003 | Lubbers et al. |
| 2003/0149436 | A1 | 8/2003 | McDowell et al. |
| 2004/0024420 | A1 | 2/2004 | Lubbers et al. |
| 2004/0030339 | A1 | 2/2004 | Wack et al. |
| 2004/0068269 | A1 | 4/2004 | Bonati et al. |
| 2004/0097941 | A1 | 5/2004 | Weiner et al. |
| 2005/0096508 | A1 | 5/2005 | Valentini et al. |
| 2005/0177166 | A1 | 8/2005 | Timm et al. |
| 2005/0216007 | A1 | 9/2005 | Woll et al. |
| 2005/0228382 | A1 | 10/2005 | Richelsoph et al. |
| 2007/0010816 | A1 | 1/2007 | Wilkinson et al. |
| 2007/0010821 | A1 | 1/2007 | Wilkinson et al. |
| 2007/0162026 | A1 | 7/2007 | Tipirneni et al. |
| 2007/0233100 | A1 | 10/2007 | Metzinger |
| 2007/0233101 | A1 | 10/2007 | Metzinger |
| 2007/0233102 | A1 | 10/2007 | Metzinger |
| 2007/0233103 | A1 | 10/2007 | Metzinger |
| 2007/0233104 | A1 | 10/2007 | Metzinger |
| 2007/0260248 | A1 | 11/2007 | Tipirneni |
| 2007/0270833 | A1 | 11/2007 | Bonutti et al. |
| 2008/0108996 | A1 | 5/2008 | Padget et al. |
| 2008/0147127 | A1 | 6/2008 | Tipirneni et al. |
| 2008/0195122 | A1 | 8/2008 | Castellvi et al. |
| 2008/0300606 | A1 | 12/2008 | Moorcroft et al. |
| 2008/0319266 | A1 | 12/2008 | Poll et al. |
| 2009/0048606 | A1 | 2/2009 | Tipirneni et al. |
| 2009/0118773 | A1 | 5/2009 | James et al. |
| 2009/0131936 | A1 | 5/2009 | Tipirneni et al. |
| 2009/0131990 | A1 | 5/2009 | Tipirneni et al. |
| 2009/0131991 | A1 | 5/2009 | Tipirneni et al. |
| 2009/0216232 | A1 | 8/2009 | Buford et al. |
| 2009/0228007 | A1 | 9/2009 | Justin et al. |
| 2009/0228008 | A1 | 9/2009 | Justin et al. |
| 2009/0254089 | A1 | 10/2009 | Tipirneni et al. |
| 2009/0254129 | A1 | 10/2009 | Tipirneni et al. |
| 2010/0121326 | A1 | 5/2010 | Woll et al. |
| 2010/0312292 | A1 | 12/2010 | Tipirneni et al. |
| 2011/0098755 | A1 | 4/2011 | Jackson et al. |
| 2011/0125189 | A1 | 5/2011 | Stoll, Jr. et al. |
| 2011/0137356 | A1 | 6/2011 | Kollmer |
| 2011/0196380 | A1 | 8/2011 | Cremer et al. |
| 2011/0295252 | A1 | 12/2011 | Tipirneni et al. |
| 2011/0295253 | A1 | 12/2011 | Bonutti et al. |
| 2012/0083742 | A1 | 4/2012 | Nelson |
| 2012/0226326 | A1 | 9/2012 | Overes et al. |
| 2012/0245630 | A1 | 9/2012 | Napolitano et al. |
| 2012/0253410 | A1 | 10/2012 | Taylor et al. |
| 2013/0012954 | A1 | 1/2013 | Paroth et al. |
| 2013/0079776 | A1 | 3/2013 | Zwirkoski et al. |
| 2013/0110168 | A1 | 5/2013 | McCormack et al. |
| 2013/0158560 | A1 | 6/2013 | Gleason et al. |
| 2013/0238036 | A1 | 9/2013 | Sinha |
| 2014/0243828 | A1 | 8/2014 | Heiney |
| 2014/0257419 | A1 | 9/2014 | Arthur et al. |
| 2017/0238983 | A1* | 8/2017 | Kukla ................ A61B 17/683 |

FOREIGN PATENT DOCUMENTS

| | | |
|---|---|---|
| EP | 3258868 | 12/2017 |
| FR | 2831419 A1 | 5/2003 |
| WO | WO1997030649 A1 | 8/1997 |
| WO | WO1998012972 A1 | 4/1998 |
| WO | WO1999011177 A2 | 3/1999 |
| WO | WO2001049189 A1 | 7/2001 |
| WO | WO2001049207 A2 | 7/2001 |
| WO | WO2001095818 A1 | 12/2001 |
| WO | WO2004045373 A3 | 5/2005 |
| WO | WO2007010185 A1 | 1/2007 |
| WO | WO2009091811 A1 | 7/2009 |
| WO | WO2009143374 A2 | 11/2009 |
| WO | WO2010034002 A1 | 3/2010 |
| WO | WO2010048473 A1 | 4/2010 |
| WO | WO2010091242 A1 | 8/2010 |
| WO | WO2010093590 A1 | 8/2010 |
| WO | WO2010096724 A1 | 8/2010 |
| WO | WO2012024465 A2 | 2/2012 |

OTHER PUBLICATIONS

Notification of Transmittal of the International Search Report for Application PCT/US2019/030654, filed May 3, 2019.

International Search Report for co-pending application PCT/US2015/058670 filed Nov. 2, 2015.

* cited by examiner

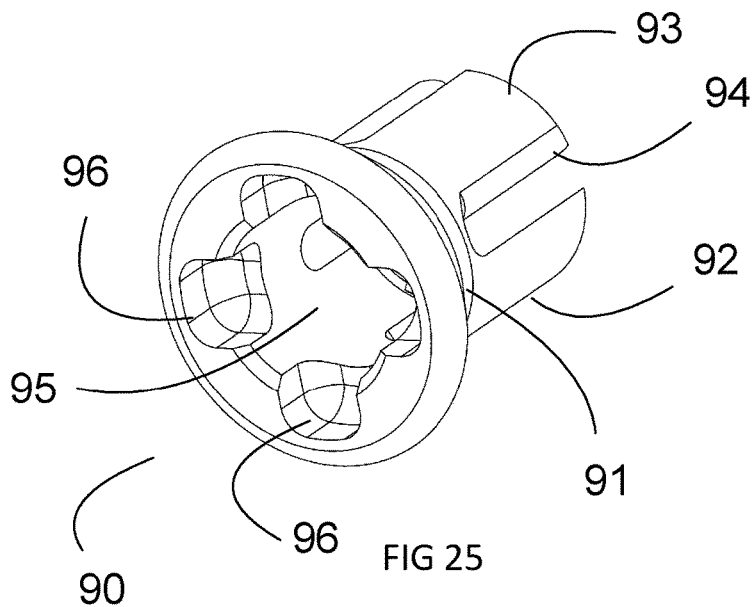
FIG 25
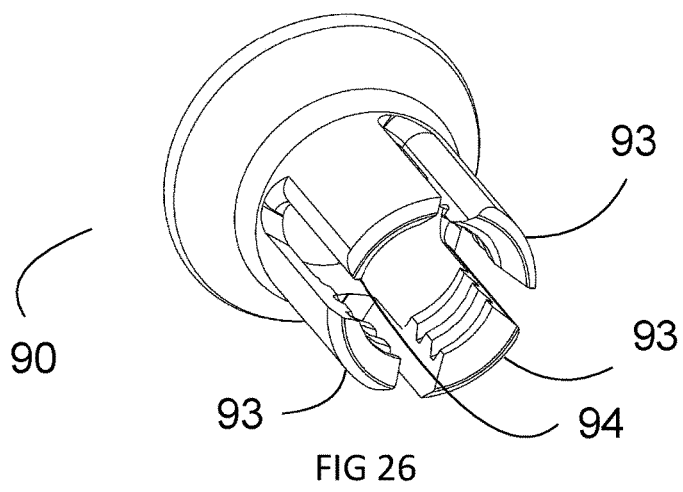
FIG 26
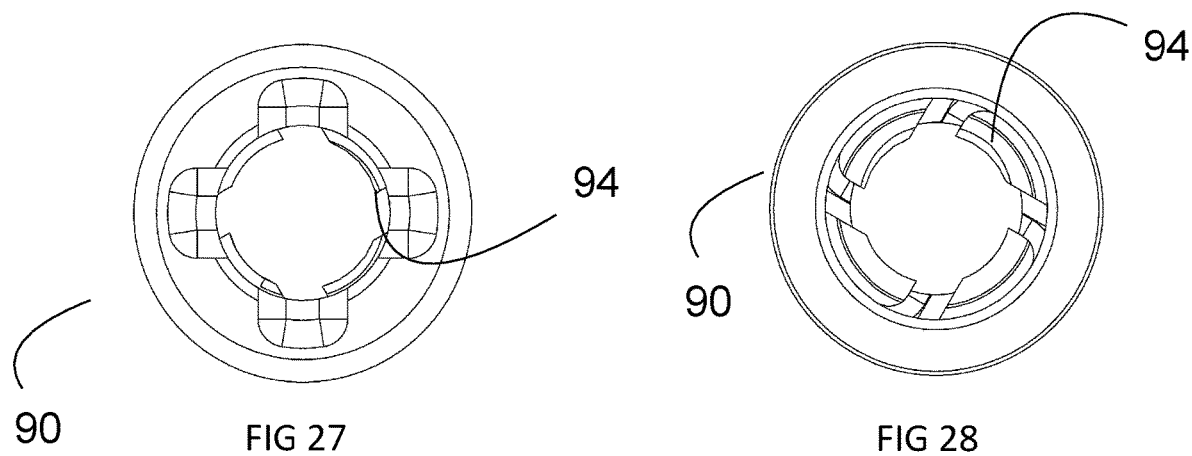
FIG 27                    FIG 28

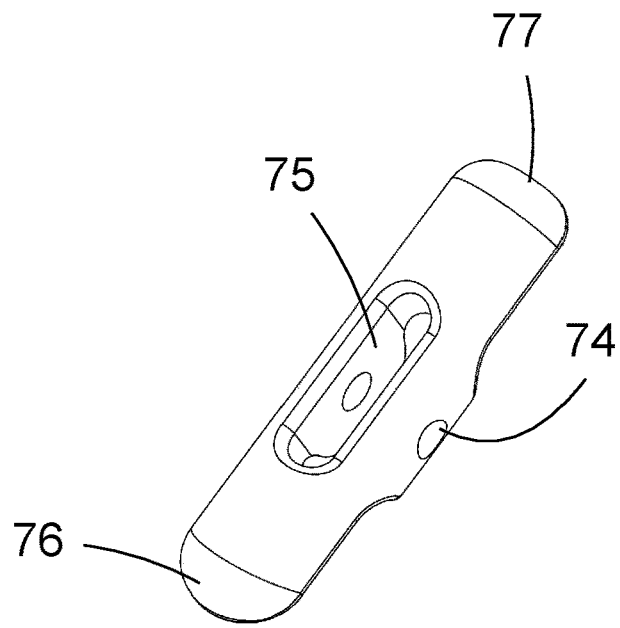
FIG 38
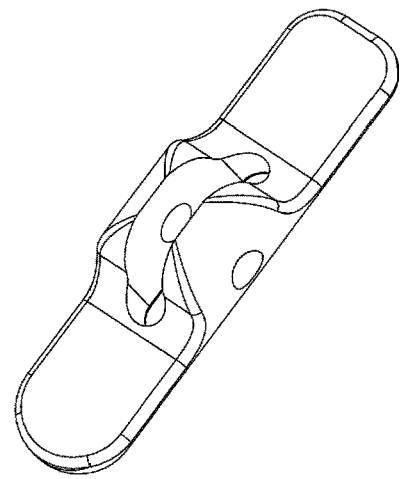
FIG 39
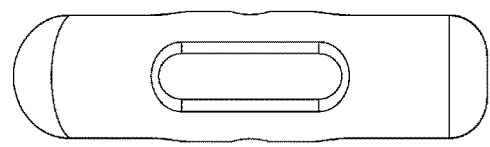
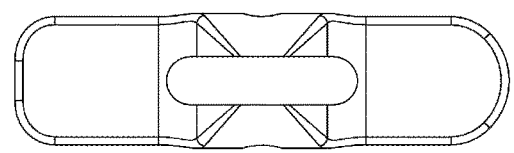
FIG 40

COMPRESSION FIXATION SYSTEM

RELATED APPLICATIONS AND PRIORITY CLAIM

This application is a 35 U.S.C. 371 National Stage application that claims priority to PCT/US2019/030654 filed on May 3, 2019, which application claims the benefit under 35 U.S.C. 119(e) to U.S. Provisional Application No. 62/667, 247 filed May 4, 2018, the entireties of which are incorporated herein by reference.

FIELD OF INVENTION AND BACKGROUND

The invention relates generally to an assembly and a compression fixation system for fixing two or more elements together and to maintain, and optionally adjust a desired degree of compression across the two or more objects. The system is suitable, for example, for connecting and compressing two or more elements selected from bones and bone fragments. The system includes a substantially linear coupling component, and an assembly that engages with an assembly-receiving portion of the coupling component in a generally coaxial orientation.

The invention is described herein below in relation to bone fractures, which is but an example of the useful application of the invention. One skilled in the art will appreciate that the assembly and compression fixation system components and the methods of use thereof as described herein can be used without undue adaptation for applications that include, but are not limited to: connecting one or more medical devices or appliances to bone; connecting one or more medical or other devices together; repairing structural components, for example, household, building and construction components such as combinations of two or more pieces of wood, concrete, supports, beams, studs, joists, columns, wall boards; and the like.

Devices and systems as disclosed herein are useful for a variety of applications, including with particularity, orthopedic fixation. There are many needs in orthopedics for the fixation of bones. In some instances, adjacent bones must be fixed together to allow for healing of damaged associated soft tissue, or to replace the function of such soft tissue, such as in the case of ligament damage between adjacent bones as well as tendon damage. In other instances, fractures of bones must be corrected by alignment, reduction of space between, and compression of the bone fragments to enable bone healing. Many approaches are known in the medical arts for achieving the attachment, fixation, and desired degrees of compression of bones and bone fragments. Generally, for example, threaded screws with and without heads, pins and rods, and wires may be used. There are challenges with all of these, which include, for example, imprecise compression and fixation, protrusion of the fixation element from bone into tissue (screw heads, twists of wires), bone loss/damage due to size of fixation element and damage to bone (for example, thread stripping of screws within bone), and costs associated with inventory to provide the number of components needed to meet size ranges of fractures.

Included in the art are several examples of compression bone fixation systems that are aimed at overcoming the shortcomings of wires and screws for bone fixation. In many instances, such systems provide fixation that overcomes some of the limitations of bone screws and wires. However, it remains a problem in the art to achieve fixation of relatively small bones using low profile fixation components that are capable of fine adjustment to placement and tensioning, are relatively simple to manipulate and are adjustable and/or removable post fixation.

Accordingly, there is a need for a fixation system that can fix, align and compress bone elements together wherein the system presents minimal risk of bone compromise and loss, and provides ease of use by the clinician, adjustability in size to minimize inventory needs, and highly reliable and precise and reversible locking to achieve reliable fixation and enable the clinically needed degree of compression between bone elements. Indeed, a particular advantage of the inventions provided herein is overcoming the challenges presented in the art with implant placement and subsequent adjustment or removal.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description:

FIG. 25 shows a top perspective view of an embodiment of a locking collet as depicted in FIG. 1 according to the disclosure;

FIG. 26 shows a bottom perspective view of the locking collet as depicted in FIG. 25;

FIG. 27 shows a top view of the locking collet as depicted in FIG. 25;

FIG. 28 shows a bottom view of the locking collet as depicted in FIG. 25;

FIG. 38 shows a bottom perspective view of an anchor comprising a toggle anchor as depicted in FIG. 1 according to the disclosure;

FIG. 39 shows a top perspective view of the anchor as depicted in FIG. 38;

FIG. 40 shows bottom and top views of the anchor as depicted in FIG. 38;

Figure 1A:
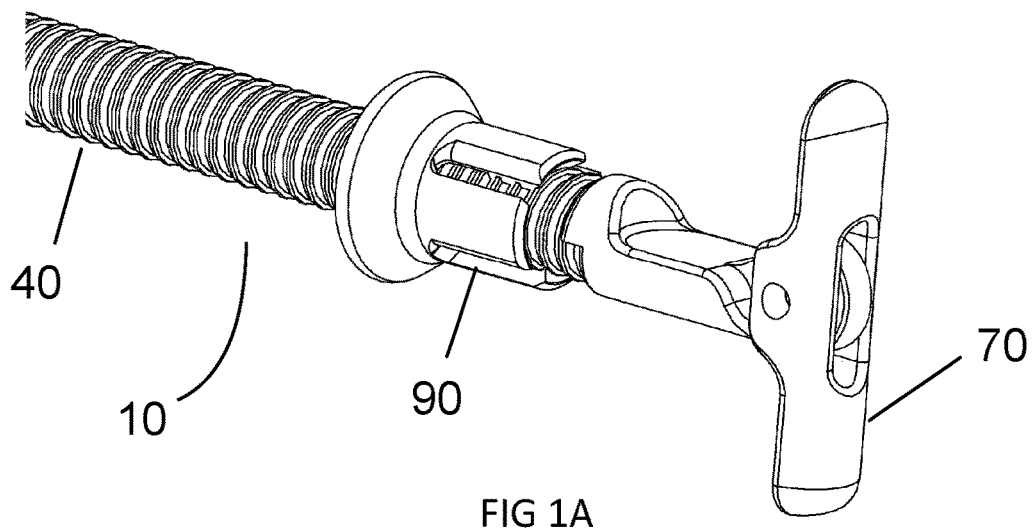
FIG. 1A shows a bottom perspective view of a first embodiment of a fully assembled compression fixation assembly according to the disclosure in a first configuration.

Features and advantages of the general inventive concepts will become apparent from the following description made with reference to the accompanying drawings, including drawings represented herein in the attached set of figures, of which the following is a brief description:

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

LIST OF REFERENCE NUMERALS

| | |
|---|---|
| 10 | assembly |
| 15 | subassembly |
| 20 | tensioning instrument |
| 21 | housing |
| 22 | housing handle |
| 23 | elongate shaft |
| 24 | engagement means |
| 25 | knob |
| 26 | cannula |
| 27 | removable handle |
| 28 | handle grip |
| 29 | knob receiver |
| 30 | system |
| 40 | coupling component |
| 41 | medial portion |
| 42 | distal portion |
| 43 | anchor fixation seat |
| 44 | anchor recess |
| 45 | thread |
| 46 | proximal portion |
| 70 | anchor |
| 71 | distal surface |
| 72 | proximal surface |
| 73 | toggle arm |
| 74 | pivot fixation point |
| 75 | fixation seat receiver |
| 76 | rounded arm terminus |
| 77 | blunt arm terminus |
| 90 | collet |
| 91 | head |
| 92 | collet body |
| 93 | leg |
| 94 | cutting edge |
| 95 | through channel |
| 96 | tool receiver |
| 97 | engagement feature |

DESCRIPTION

This description describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts will now be described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care. More broadly, in connection with non-medical uses of the inventions described herein, the term refers to a user of one or more components of the compression fixation system.

Unless otherwise indicated, all numbers expressing quantities, properties, and so forth as used in the specification and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

Use of Compression Fixation System

Generally, in accordance with the embodiments described herein and depicted in the drawings, the invention is directed in various aspects to assemblies, systems, components, instruments, and methods for fixing and/or compressing elements along a generally rectilinear path, using an assembly that includes at least one of each of a coupling component, an anchor and a collet. As described herein, components of the assembly engage in a generally coaxial orientation, such that, at least a portion of the coupling component comprises a generally rectilinear configuration and is adapted to engage with the collet. In the various embodiments, at least the coupling component and collet components of the assembly may be engaged with one another and locked into fixed engagement using a tensioning instrument. In various embodiments, as described herein, the assemblies when engaged and locked are useful to secure two or more elements together, the elements selected from bones, plates, biomedical textiles, and other medical devices, whereby a combination of two or more such elements are secured together. In representative examples, two or more bone portions may be locked together with an assembly.

In certain particular embodiments, the system enables fixation of two or more traumatized, fractured, deformed, and/or otherwise displaced bones or bone fragments. Embodiments of compression fixation systems are disclosed herein that significantly enhance the surgical techniques for repairing damaged bones, such as fractured phalangeal and metatarsal bones, and provide improved and superior performance in the achievement and maintenance of fixation and desired bone compression as compared with use of conventional wires and screws. In one example of use, a metatarsal fracture may be fixated with an embodiment of a compression fastening system according to this disclosure, wherein an untrimmed coupling component is passed through two or more bone fragments of the metatarsal bone to be joined, the coupling component extending proximally out of an upper surface of the fractured bone, with a collet engaged with the coupling component and secured into contact with the proximal bone surface. An anchor is oriented opposite from the collet and on the distal side of the distal (lower) bone fragment, such that tensioning of the coupling component between the collet and the anchor achieve locked fixation between the bone and the collet, facilitated by one or more cutting edges on the collet.

In contrast to screws, certain embodiments of the assembly and system described herein enable flexible and adjustable orientation and positioning of adjacent bones to be fixed, which cannot be achieved using conventional rigid screws. In particular, the adaptable sizing of the coupling components enables customized sizing without the need to have a wide array of sizes on hand such as is required when using screws. That is, the coupling components are adaptable for use with different collets and may comprise different anchors and the coupling components can be adjusted in a length dimension, thus obviating the need for alternate lengths. And in another example, in contrast to conventional K (Kirschner) wires which are also used in the medical arts for bone fixation whereby they are fixed into compression via crimping and twisting, certain embodiments of the systems described herein enable precise compression that can be finely and selectively adjusted without compromise to the healing bone or to the fixation system components. Moreover, the instant disclosure enables use of ancillary fixation devices such as flanges and plates that can be positioned and locked to bone using the collets described herein.

Significant benefits can be realized in connection with surgical use of the fixation system, including, but not limited to optimized patient experience and outcome as a result of controlled and precise compression to enhance healing and minimized bone damage/loss; improved time efficiency during surgery; and enhanced options for implant selection and customization. Time savings during surgery are realized in comparison to the current state of the art due to the elimination of need to precisely measure for and select a specific length of implant; the instant disclosure provides a system that can be customized in size without any compromise in fixation. Cost savings can also be realized through reduction of required implant sizes; the instant disclosure provides a system in which one implant fits all and can be easily sized to the specific patient, resulting in a significant reduction in the number and size of devices that must be stocked.

While the examples provided herein pertain to the fixation/compression of bone material, it will be appreciated that other materials of relevance to the body, including biological and non-biological, implanted and non-implanted, can be fixed together and as desirable, compressed using the inventions disclosed herein. Examples herein include use of the compression fixation system for reduction, alignment, fixation and/or compression of bone fragments such as in the phalanges and metatarsal bones. Of course, it will be appreciated by one skilled in the art that the inventive components can be used in connection with most types of fractures, particularly such fractures that are typically treated by percutaneous insertion of pins and wires and screws. Further, the system is suitable for use with other bone element fixation indications.

Compression Fixation Assembly

Figure 1B:
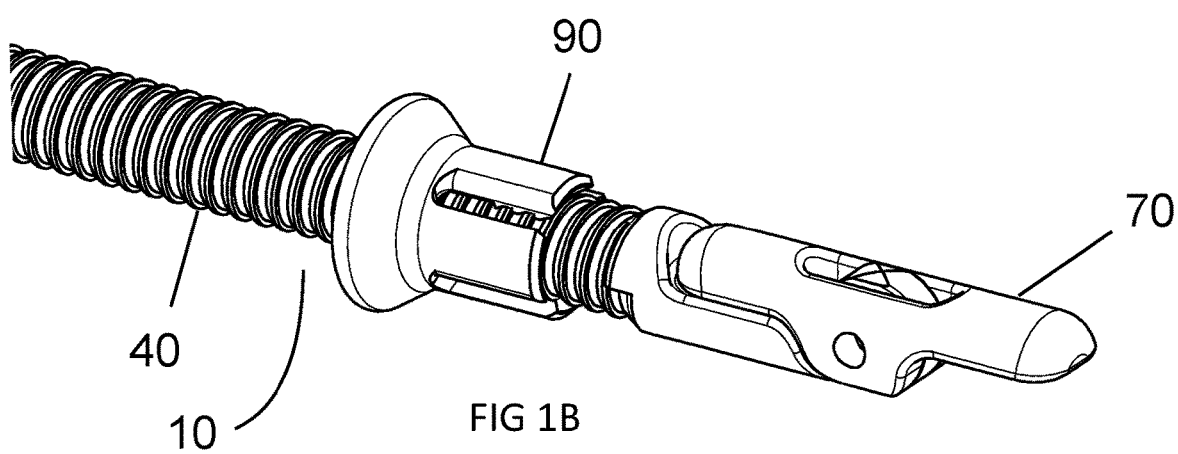
FIG. 1B shows a bottom perspective view of a first embodiment of a fully assembled compression fixation assembly according to the disclosure in a second configuration.
Figure 2:
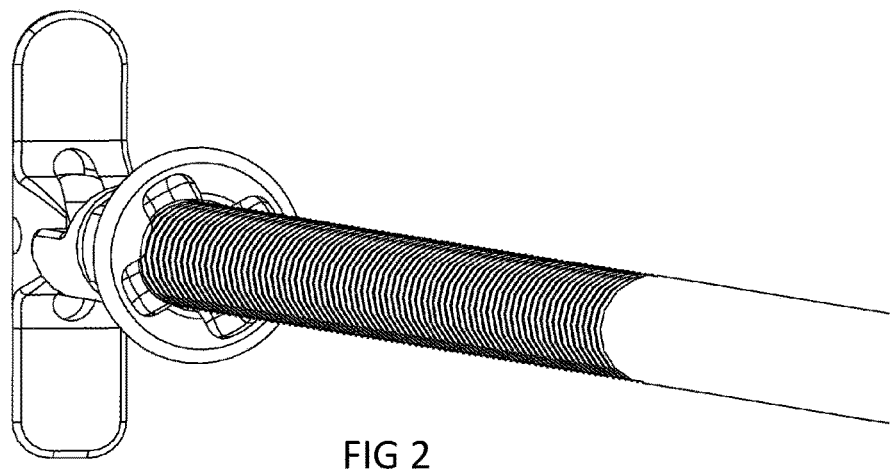
FIG. 2 shows a top perspective view of the compression fixation assembly as depicted in FIG. 1.
Figure 3:
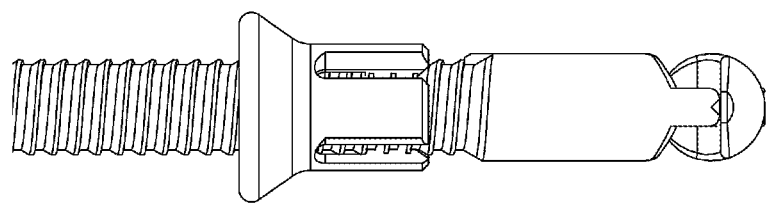
FIG. 3 shows a first side view of the compression fixation assembly as depicted in FIG. 1.
Figure 4:
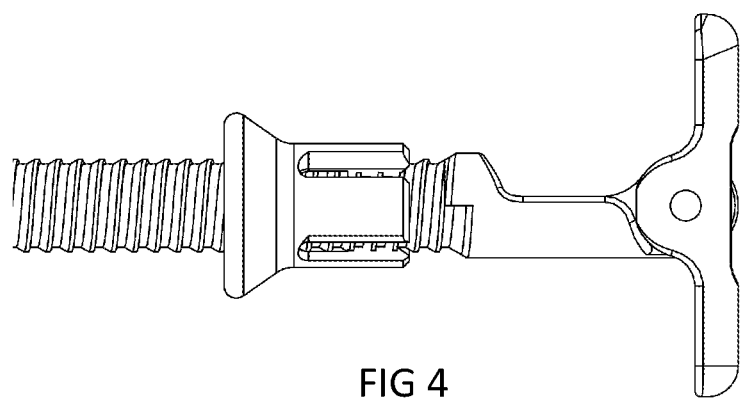
FIG. 4 shows a second side view of the compression fixation assembly as depicted in FIG. 1.
Figure 5:
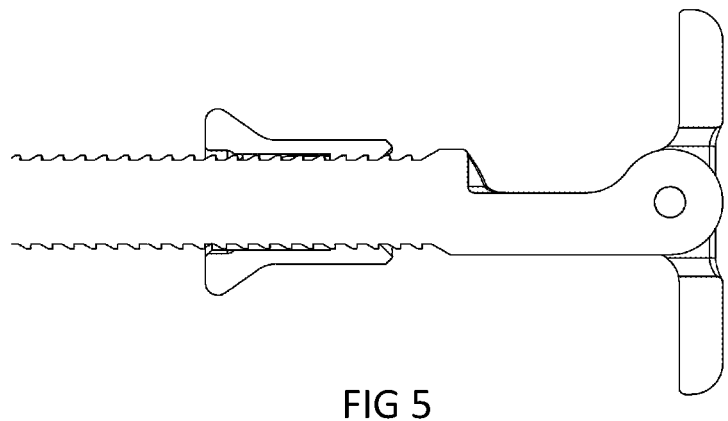
FIG. 5 shows a side view in cross section of the compression fixation assembly as depicted in FIG. 4.
Figure 6:
FIG. 6 shows on the left and right, respectively, bottom and top views of the compression fixation assembly as depicted in FIG. 1.
Figure 7:
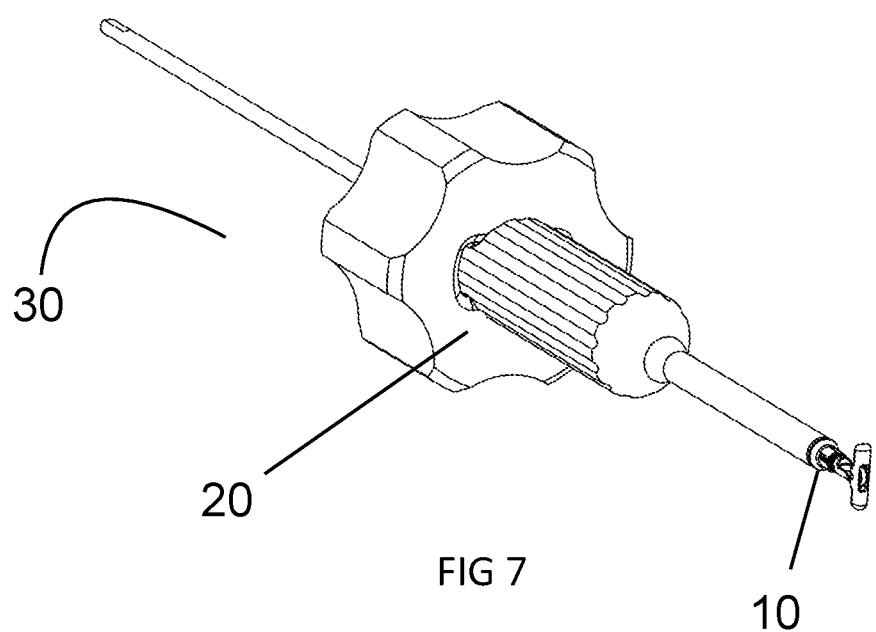
FIG. 7 shows a bottom perspective view of a first embodiment of a fully assembled compression fixation system including an embodiment of an assembled compression fixation assembly as depicted in FIG. 1 engaged with an embodiment of a tensioning and locking instrument according to the disclosure.
Figure 8:
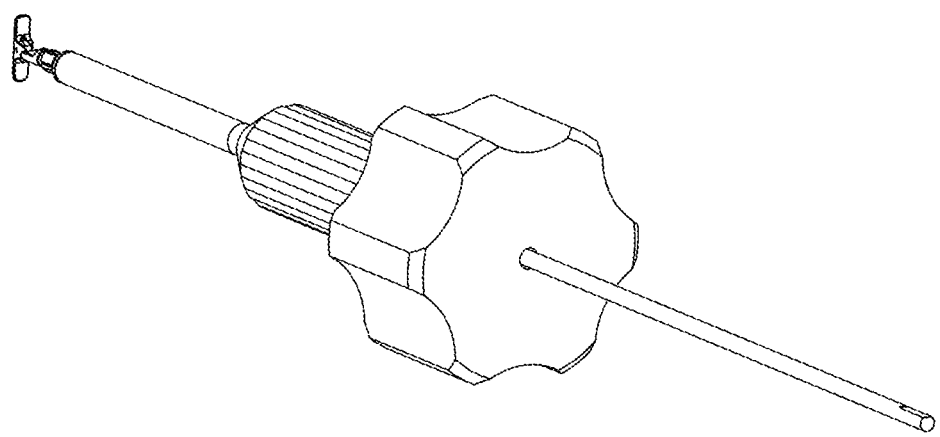
FIG. 8 shows a top perspective view of the compression fixation system as depicted in FIG. 7.
Figure 9:
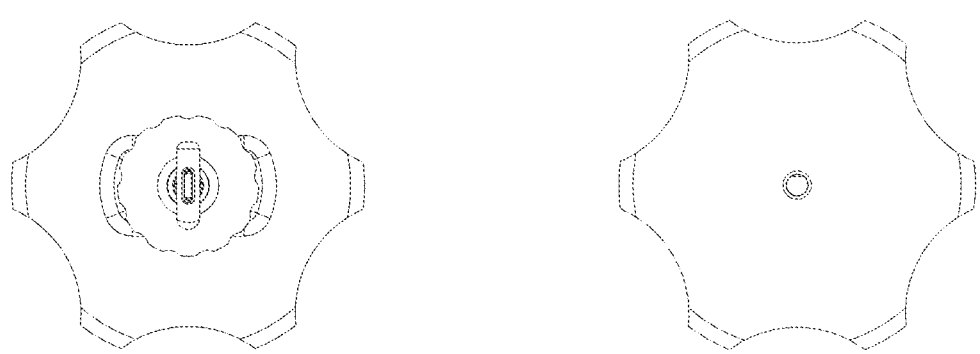
FIG. 9 shows on the left and right, respectively, bottom and top views of the compression fixation system as depicted in FIG. 7.
Figure 10:
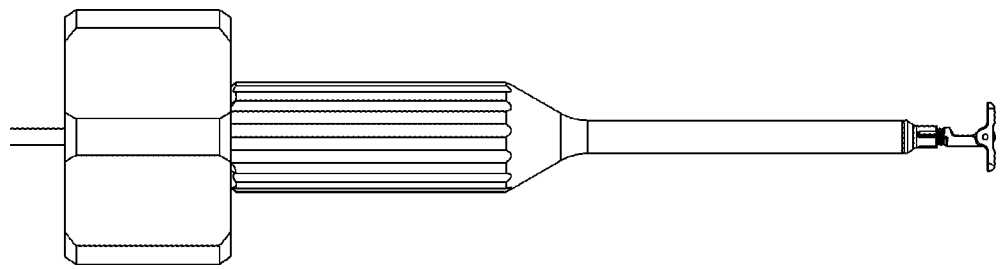
FIG. 10 shows a first side view of the compression fixation system as depicted in FIG. 7.
Figure 11:
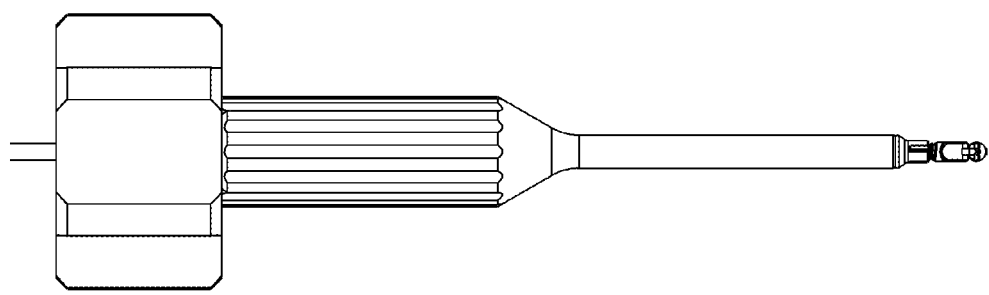
FIG. 11 shows a second side view of the compression fixation system as depicted in FIG. 7.
Figure 12:
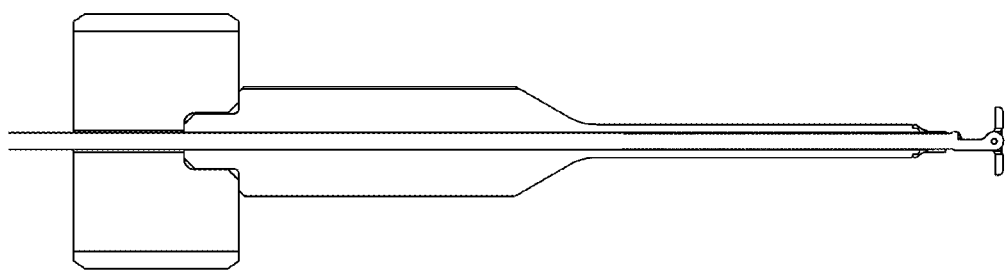
FIG. 12 shows a side view in cross section of the compression fixation system as depicted in FIG. 7.
Figure 13:
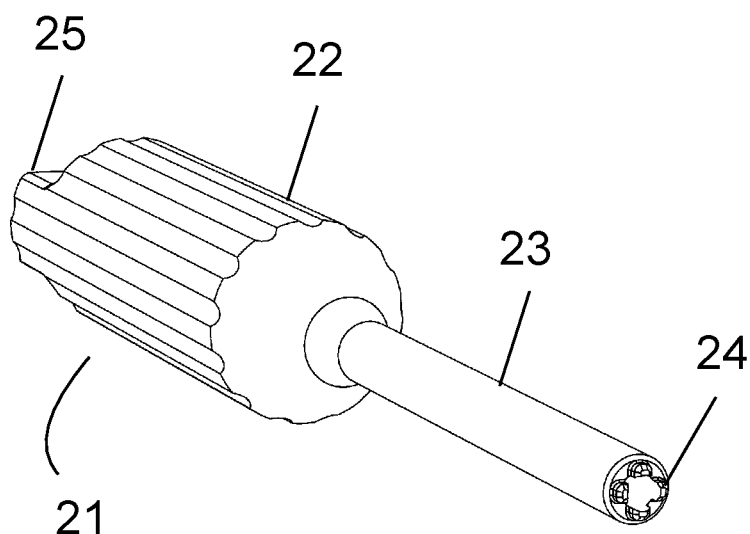
FIG. 13 shows a bottom perspective view of a tensioning and locking instrument according to the disclosure as depicted in FIG. 7.
Figure 14:
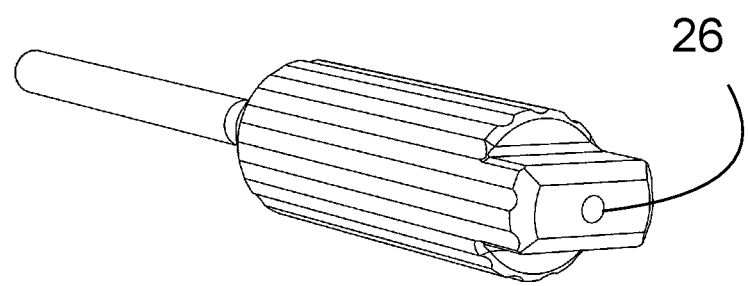
FIG. 14 shows a top perspective view of the tensioning and locking instrument as depicted in FIG. 13.
Figure 15:
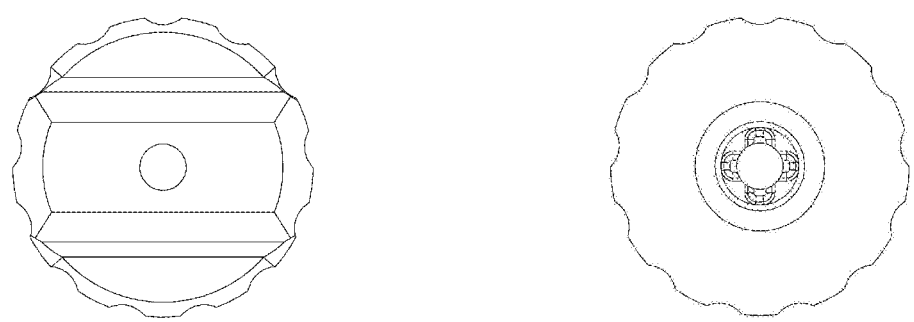
FIG. 15 shows on the left and right, respectively, bottom and top views of the tensioning and locking instrument as depicted in FIG. 13.
Figure 16:
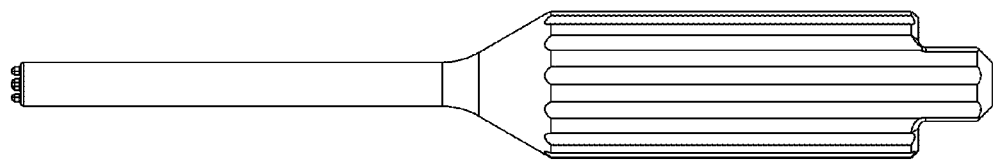
FIG. 16 shows a first side view of the tensioning and locking instrument as depicted in FIG. 13.
Figure 17:
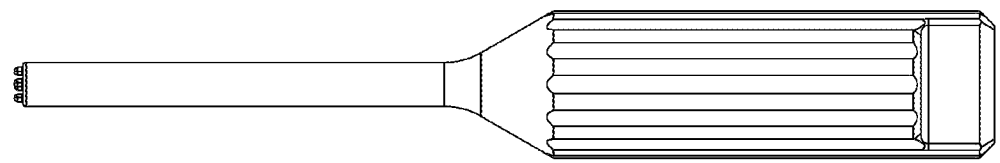
FIG. 17 shows a second side view of the tensioning and locking instrument as depicted in FIG. 13.
Figure 18:
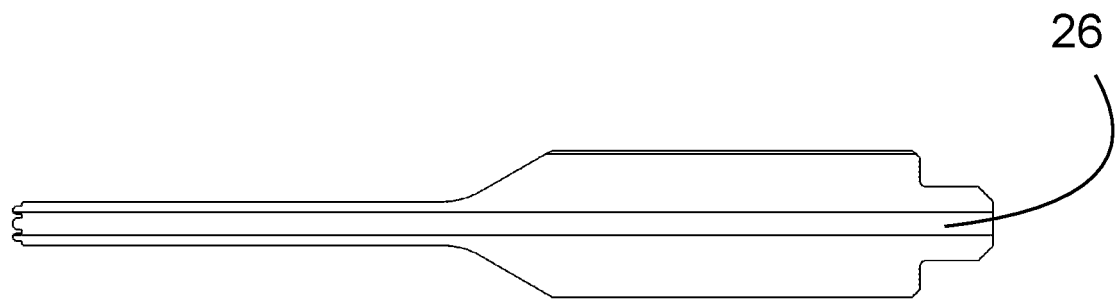
FIG. 18 shows a first side view in cross section of the tensioning and locking instrument as depicted in FIG. 13.

Referring now to the drawings, FIG. 1-FIG. 6 show alternate views of a fully assembled compression fixation assembly 10 embodiment according to the disclosure. Referring to FIG. 1, the assembly 10 includes a coupling component 40, a collet 90 and a toggle anchor 70, wherein the collet has a through channel for receiving a coupling component 40 to achieve locking fixation with the coupling component 40. According to the various embodiments, the collet 90 is constructed to slide over at least a first end of the coupling component 40 and can be held stably on the coupling component 40 in a friction (engaged but not locked) configuration to enable positioning relative to the elements to be fixed, and can be actuated to achieve a locked configuration by engagement with the elements to be fixed. In various exemplary embodiments of the assembly, as shown in the drawings, inter-engaging collet 90, toggle anchor 70 and coupling components 40 cooperate along a shared axis and inter-engage together, and with elements such as bone, to form an assembly.

Coupling Component

Figure 32:
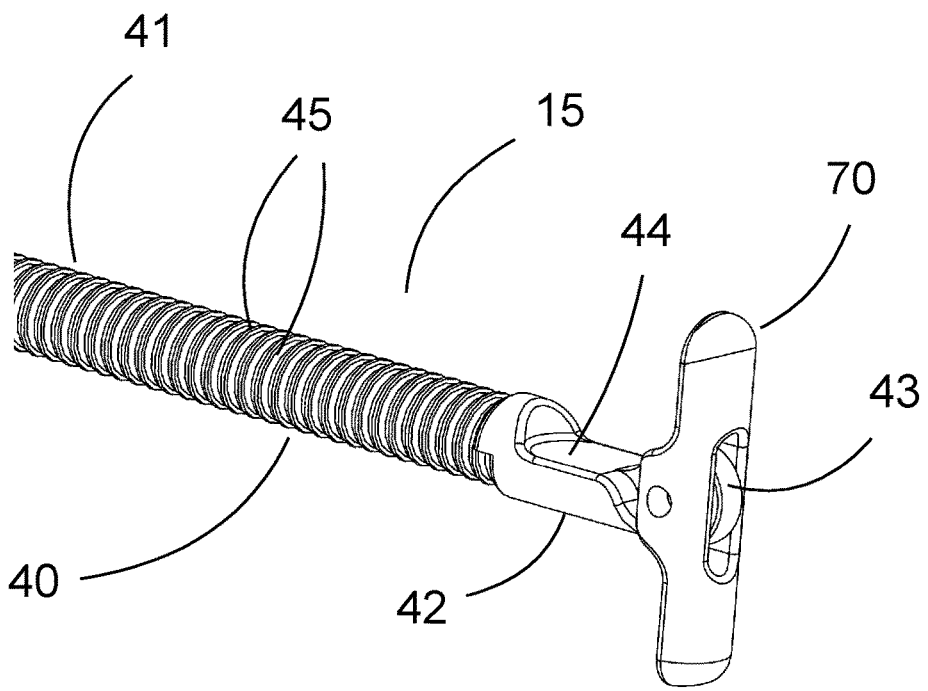
FIG. 32 shows a bottom perspective view of a sub-assembly of the compression fixation assembly as depicted in FIG. 1, the sub assembly including an embodiment of a coupling component and an embodiment of an anchor comprising a toggle anchor according to the disclosure.
Figure 33:
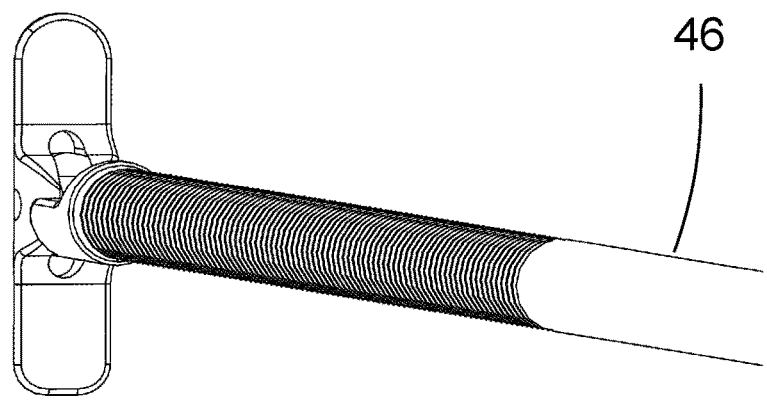
FIG. 33 shows a top perspective view of the coupling component and anchor sub-assembly as depicted in FIG. 32.
Figure 34:
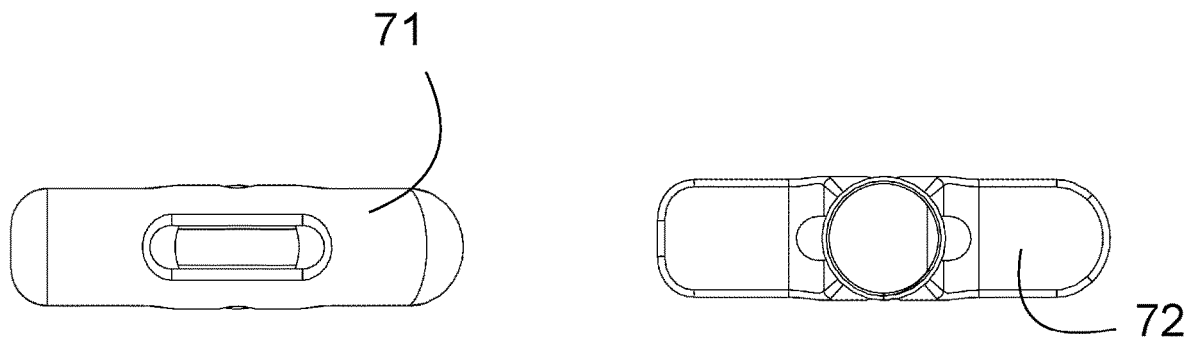
FIG. 34 shows a bottom view of the coupling component and anchor sub-assembly as depicted in FIG. 32.
Figure 35:
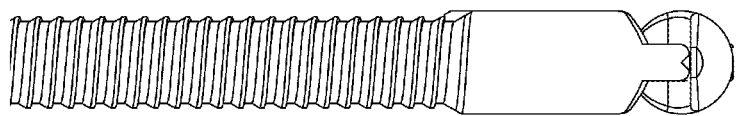
FIG. 35 shows a first side view of the coupling component and anchor sub-assembly as depicted in FIG. 32.
Figure 36:
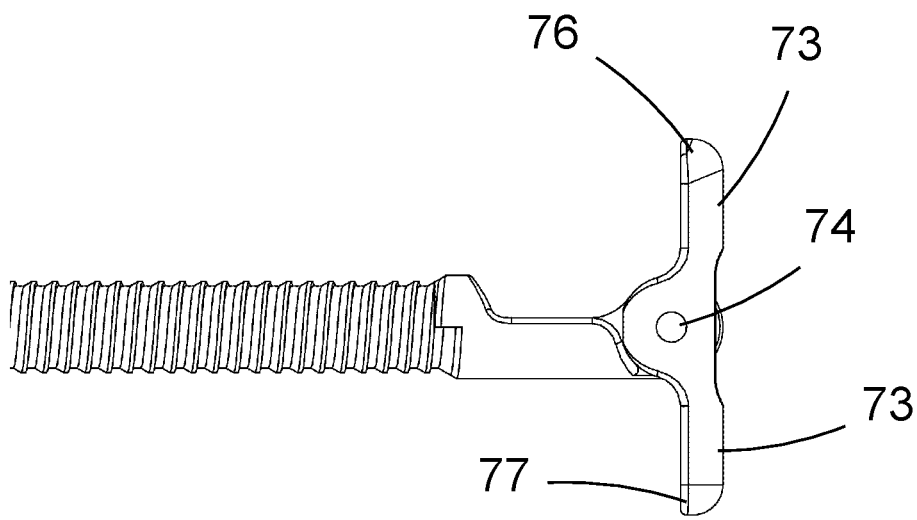
FIG. 36 shows a second side view of the coupling component and anchor sub-assembly as depicted in FIG. 32.
Figure 37:
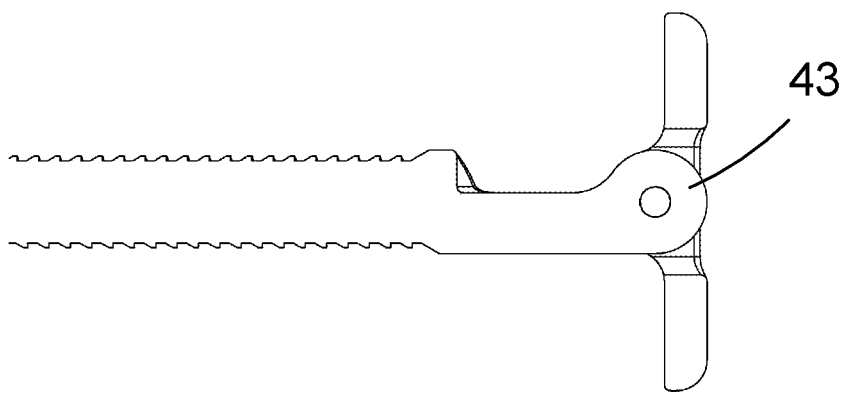
FIG. 37 shows the second side view in cross section of the coupling component and anchor sub-assembly as depicted in FIG. 32.
Figure 41:
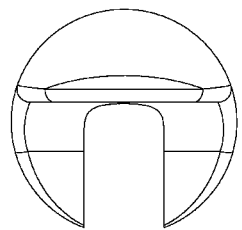
FIG. 41 shows a first side view of the anchor as depicted in FIG. 38.
Figure 42:
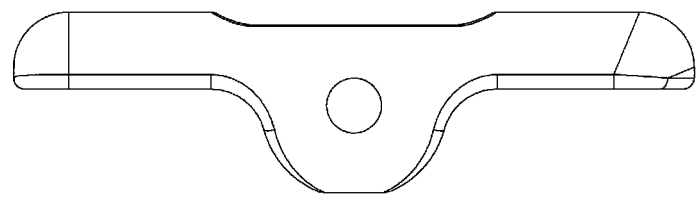
FIG. 42 shows a second side view of the anchor as depicted in FIG. 38.
Figure 43:
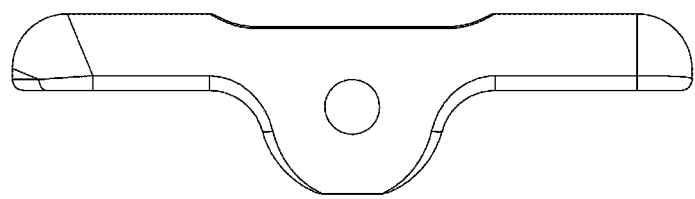
FIG. 43 shows a third side view of the anchor as depicted in FIG. 38.
Figure 44:
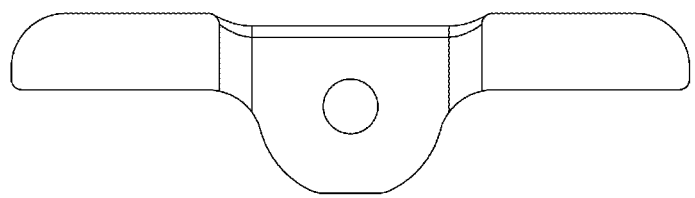
FIG. 44 shows the second side view in cross section of the anchor as depicted in FIG. 38.

Referring again to the drawings in FIG. 32 and FIG. 33, alternate views of an embodiment of a coupling component 40 are shown in a subassembly 15 with a toggle shaped toggle anchor 70. In the depicted embodiment, the coupling component 40 comprises a thread 45 along at least a portion of its length within the medial portion 41, the thread 45 is adapted for engaging with one or more complimentary threads on the inner surface of the locking collet 90. In some embodiments, the thread 45 on the coupling component 40 may include along all or a portion of its length indicia to enhance visibility of the thread 45. Such indicia may include laser or other means of deposited coloration that may be one of solid coloration, varied colors and other patterning.

In various embodiments, at least the medial portion 41 of the coupling component 40 is substantially rectilinear, and cylindrical. And the coupling component 40 also comprises at a second end, intended to be most proximal to the operator, a proximal portion 46 that may or may not be adapted for engagement with a collet 90. In some embodiments, one or more of each of the distal portion 42, medial portion 41 and proximal portion 46 of the coupling component 40 is adapted to be manipulated into a bent or twisted configuration by the operator for optimal engagement and shape conformity with the two or more elements to be fixed.

One of ordinary skill will appreciate that the depicted coupling component 40 can be provided in variable lengths, with or without curves or bends, with or without surface texture and/or surface features. Moreover, while the depicted coupling component 40 is generally cylindrical in shape from the proximal end and terminates at the exemplary toggle anchor 70 having a toggle shape, one of ordinary skill will appreciate that the shape of the coupling component 40 may be other than cylindrical (i.e., the cross section may be other than circular). Thus, in some alternate embodiments, the coupling component 40 may have a cross section that is selected from one of the following non-limiting examples, including, scalloped, star shaped, hexagonal, square, and ovoid. Likewise, the coupling component 40 may be uniform in cross-sectional shape and width along its entire length, or it may comprise regions that vary and include combinations of different cross-sectional shapes, widths/diameters, and textures.

In some alternate embodiments, the coupling component 40 may have a diameter that permits cannulation through at least a portion of the coupling component 40. In some examples such embodiments may include cannulated bone wires and pins. In other such embodiments, examples include tubes, conduit, pipes, and other substantially hollow components that are suitable to receive an assembly along at least a portion of the coupling component 40 that is rectilinear.

It will be appreciated that any particular portion of a coupling component 40 which may be substantially rectilinear for receiving an assembly may be cylindrical or otherwise shaped and may be smooth or have any one of a variety of surface features such as grooves or notches and textures that comprise knurling or other non-smooth texturing. Further, while the exemplary embodiment of the coupling component 40 shown in the drawings terminates as a cylinder at the proximal end 46, there may be alternate shapes and features at the proximal end that are suited for engagement with a tool or instrument. Thus, in some non-limiting examples, the coupling component 40 may comprise at its proximal end 46 a hemispherical, conical or frustoconical feature, or a star, scallop or hex cross-section, or combinations of these.

It will be appreciated that in some alternate embodiments, the coupling component 40 may alternatively comprise at least in the medial portion 41 any of a variety of surface features for engagement with complimentary features in the collet 90, for example but not limited to features including two or more threads, surface knurling, and a series of spaced circumferential grooves. In some such embodiments wherein at least the medial portion 41 includes grooves, the number and spacing of the grooves may vary such that there are more or fewer, the grooves are narrower or wider, deeper or shallower, and are equidistant or variably spaced. In accordance with such embodiments, the grooves are adapted for receiving one or more ridge features on the inner surface of a locking component, such as a locking collet 90.

In addition, in alternate embodiments, a coupling component 40 may comprise other surface features to either enhance sliding between a collet 90 and the coupling component 40 or to enhance friction there between, or combinations of these. Further, such textures and features may cover the full length of the coupling component 40 or may vary along the length of a coupling component 40 to differentially enhance surface contact with various instruments, components, and bone.

The coupling component 40 is generally elongate and is configured comparable to known fixation devices selected from wire and other bone pins and similar rod type devices, such as, for example K-wire. The coupling component 40 is adapted at a first end, intended to be most distal to the operator, with a distal anchor portion 42 for fixation within or on a distal outer surface of an element, for example a first bone element. In some embodiments, as depicted in the drawings, the distal anchor portion 42 is adapted with an anchor fixation seat 43 for engagement with a toggle anchor 70.

The distal anchor portion 42 of the coupling component 40 comprises an toggle anchor 70 that is selected from any of a number of anchors known in the art, and generally selected from anchors (i) adapted to engage with and remain substantially within and anchor to a bone, and (ii) that extend through bone and are adapted to engage with an outer surface of one or more of a bone, a bone fragment, a plate, another non-bone material that is intended to be held adjacent to a bone element. Some examples of anchors that are adapted to engage with and remain substantially within and anchor to a bone include self or non-self-tapping threads, and bone engagement features that can engage by press fitting such as keels, ribs and fins. Some example anchors that extend through bone and are adapted to engage with an outer surface include coils, barbs, and toggles.

According to the embodiments shown in the drawings, a toggle anchor 70 having a generally toggle shape is affixed to the anchor fixation seat 43. In some particular embodiments, as shown in FIG. 32, the distal anchor portion 42 of the coupling component 40 also includes an anchor recess 44 for retaining all or a portion of the toggle anchor 70 when it is rotated into an orientation that enables passage through a cannula or other passage, such as through a through channel in a collet or a bone hole, or the like. As further described herein, other anchors may be affixed via the anchor fixation seat 43.

Anchor

Referring again to the drawings, FIG. 32-FIG. 37 depict alternate views of an embodiment of a subassembly 15 that includes a coupling component 40 and toggle anchor 70 according to the disclosure, and FIG. 38-FIG. 44 depict alternate views of a toggle anchor 70. According to the depicted embodiment, the toggle anchor 70 is a toggle, which is pivotal around an axis defined by a pivot fixation point 74 that is in communication with the coupling component 40 at the anchor fixation seat 43 with an engagement feature that includes a pin (not shown) insertable through each of the pivot fixation point 74 and the anchor fixation seat 43 of the coupling component 40. The toggle anchor 70 has a generally hemicylindrical shape with a body formed of toggle arms 73 each having a terminus that is one of blunt and rounded 76, 77. As shown, at least one toggle arm 73 terminus may be blunt/squared 77 relative to the other which is rounded 76. Of course, in other embodiments, both termini may be rounded, or both may be blunt/squared, or may be another shape such as square or conical or frusto-conical, or combinations of these. In accordance with the non-limiting depicted embodiment, the toggle anchor 70 has a semicircular cross-sectional shape.

Referring again to the drawings, as shown in FIG. 1, the long axis of the toggle anchor 70 in a deployed state is oriented perpendicular to a long axis of the coupling component 40, and in a closed state is oriented generally parallel to the long axis of the coupling component 40 with an end of the toggle anchor 70 resting in the toggle seat 44, indicated in FIG. 32. The toggle anchor 70 also includes a distal surface 71 and a proximal surface 72 (the references distal and proximal, as previously described herein, being with respect to the position of a user who is deploying the assembly relative to bone and or other elements), and includes a fixation seat receiver 75 for engagement with the anchor fixation seat 43 of the coupling component 40. In the depicted embodiment, the toggle anchor 70 is pivotal in only one direction, the coupling component 40 being adapted with an anchor recess 44 to receive at least a portion of a toggle arm 73 of the toggle anchor 70, whereby the overall cross-sectional area of the closed toggle anchor 70 generally matches the cross-sectional area of at least the distal portion 42 of the coupling component 40 allowing a minimal profile for insertion into bone.

Referring again to FIG. 32, a distal to proximal end perspective view of the subassembly 15 is shown with a toggle anchor 70 at the distal end of the coupling component 40. In each of FIG. 32 and FIG. 33 the toggle anchor 70 is in a securement configuration, such that the toggle of the toggle anchor 70 is pivoted so that it is aligned perpendicular to the long axis of the coupling component 40 to enable securement against an element such as a bone through which the assembly is passed. In the insertion configuration (not shown) the toggle anchor 70 is pivoted 90 degrees so that its long axis is in line with the axis of the coupling component 40, for insertion into the bone and allowing clean exit from a hole in the bone that traverses the bone from a proximal to a distal portion of the bone.

Actuation of the pivot feature of the toggle anchor 70 rotates its position so that it is perpendicular to the axis of the coupling component 40 and is deployed to operate as a toggle anchor 70, thereby preventing back out of the coupling component 40 from the bone. According to the instant embodiment shown in FIG. 2, the toggle as shown attaches to and engages with the coupling component 40 in a nested cantilever configuration, whereby actuation to close the toggle involves pivoting around a central pivot axis that is on the terminal end along the axis of the coupling component 40.

The cantilever design of the toggle enables actuation of the toggle against tissue that is distal to the most distal bone fragment to facilitate engagement of the toggle anchor 70 with the bone for achieving joining and fixation between the bone fragments. Of course, it will be appreciated that other mating configurations of a toggle and coupling component 40 are possible, and that the depicted anchor fixation seat 43 and anchor recess 44 may have other shapes and configurations and are not intended to be in any manner limiting.

Figure 45:
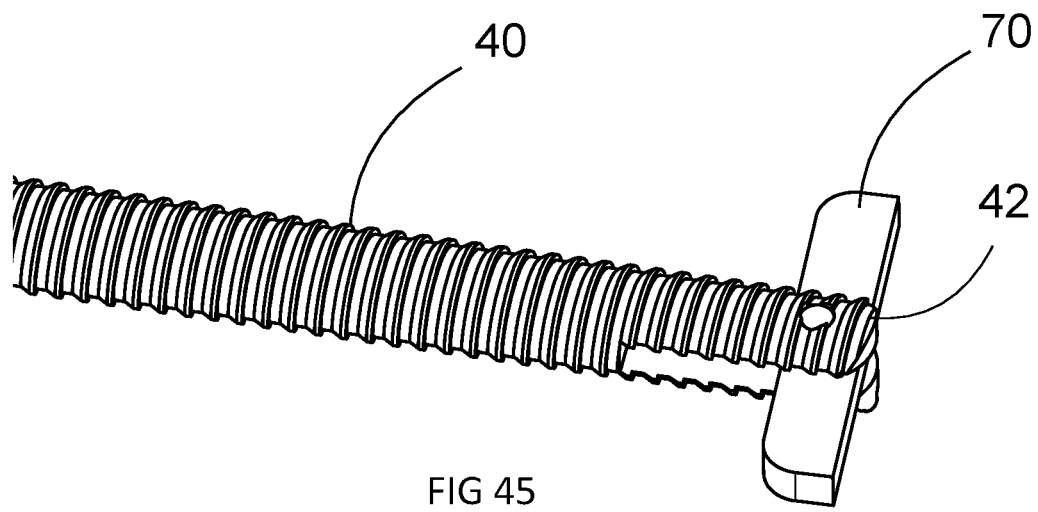
FIG. 45 shows a bottom perspective view of an alternate embodiment of a coupling component and anchor sub-assembly of a compression fixation assembly according to the disclosure.
Figure 46:
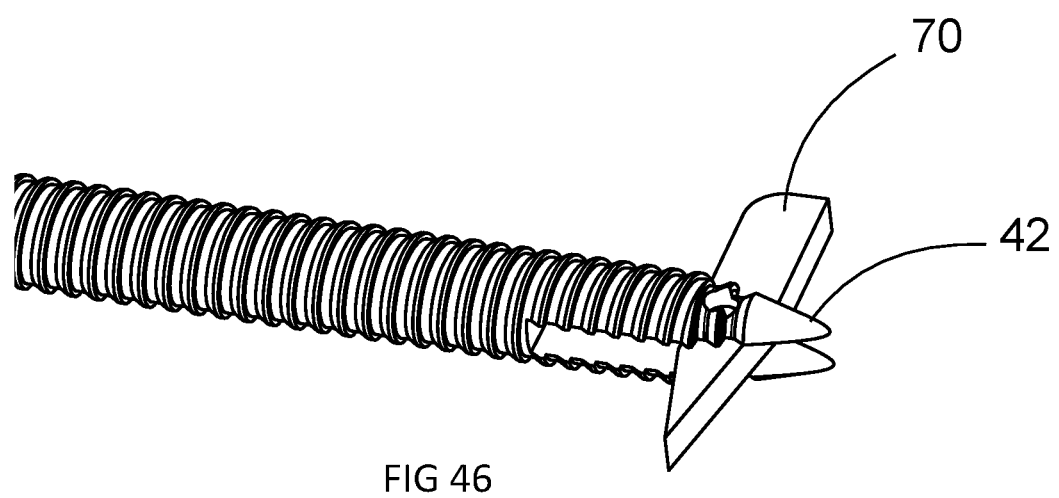
FIG. 46 shows a bottom perspective view of an alternate embodiment of a coupling component and anchor sub-assembly of a compression fixation assembly according to the disclosure.

In alternate embodiments as disclosed herein, the toggle anchor 70 is attached in an alternate manner whereby the coupling component 40 is split at its end, and the toggle rotates within the split end of the coupling component 40. And in accordance with the alternate embodiment, in one example, the toggle anchor 70 is attached to the distal end of the coupling component 40 using a through pin that snap fits or may alternatively be welded or soldered in place. Thus, as mentioned herein above, the coupling component 40 may in some such embodiments include at its distal anchor portion 42 a thread that continues to the terminus of the distal anchor portion 42, and may include a longitudinal slit or slot through the distal anchor portion 42 that extends along a portion of the length toward the proximal end. The slot may be adapted to provide a seat for the engagement of the toggle anchor 70. Referring now to FIG. 45 and FIG. 46, the depicted embodiments of the coupling component 40 include at the distal anchor portion 42 a thread that continues to the terminus of the distal anchor portion 42, and includes a longitudinal slit or slot through the distal anchor portion 42 and extending along a portion of the length toward the proximal end. The slot is adapted to provide a seat for the engagement of the toggle anchor 70. As shown in the drawings, the toggle anchor 70 is affixed via a fastener to the distal anchor portion 42 and is situated to be pivoted into alignment with the long axis of the coupling component 40 to allow passage into bone, and may be pivoted 90 degrees to an orientation that is roughly perpendicular to the long axis of the coupling component 40 for engagement and retention. FIG. 45 and FIG. 46 show alternate examples of this embodiment, wherein the distal anchor portion 42 is one of radiused and sharpened.

One of ordinary skill will understand that yet in other embodiments, the toggle may be attached by any one of other possible means.

It will be appreciated by one of skill in the art that the overall shape of the depicted toggle anchor 70 is not limiting, and that other shapes and configurations are possible, including having a generally circular, square or other cross-sectional shape. In addition, a toggle anchor need not be substantially planar as is depicted in the drawings and may instead be curved along one or both of the short and long axes. And each of the toggle arms 73 may have the same or different shapes. Thus, in some embodiments, a toggle anchor 70 may be crescent or semicircular in shape or may be scalloped or rippled or otherwise shaped or textured on at least one surface.

Shape Transforming Anchors

In the various embodiments, each of the components of the assembly 10 may be formed of any of a variety of materials including metals, shape memory metals, plastics and combinations of these. In some particular embodiments, at least the toggle anchor 70 may be formed of any of a variety of materials as may be described herein, and particularly selected from formed polymers, metals and combinations of these. In some particular embodiments, the toggle anchor 70 may be formed of a memory shape metal (such as but not limited to Nitinol). In accordance with such embodiments, the toggle anchor 70 may be formed to have a conformation that transforms at body temperature, and in some particular embodiments, such transformation may be functional to enhance the compression between elements that are engaged with a compressive assembly. For example, an toggle anchor 70 may be generally planar at temperatures below a threshold biological temperature (e.g., 98.6 degrees F.), and may transform into a crescent or arcuate shape in the body, wherein the distal surface 71 transforms from planar to convex and the proximal surface 72 that is in contact with the distal coupled elements transforms from planer to concave, effectively drawing the coupling component 40 into greater compression between a collet 90 affixed on the proximal surface 72 of the coupled elements and the transformed toggle anchor 70 on the distal side of the coupled elements.

Collet

Referring again to the drawings, FIG. 1 shows an exemplary assembly that includes a coupling component 40, collet 90 and toggle anchor 70, with the coupling component 40 inserted through a through channel 95 of the collet 90, the toggle anchor 70 in the form of a toggle in the open configuration.

Referring again to the drawings, FIG. 25-FIG. 31 show alternate views of an embodiment of a collet 90. In the depicted embodiment of the collet 90, shown, for example, in FIG. 25, the collet is generally cylindrical, having a central through channel 95 that is cylindrical and adapted to receive the coupling component 40. The collet 90 includes an collet expandable body 92, the collet body 92 including legs 93 that are separated by a slit, at least one leg including a cutting edge 94, and a generally cylindrical proximal head 91 that is adapted with one or more tool receiver 96 features, which in the depicted embodiment are arrayed circumferentially around the head 91 on a proximal surface 72 and adapted for engagement with a tensioning instrument 20 to drive the collet 90 along the coupling component 40. In some embodiments the collet 90 includes two legs 93 and in other embodiments, such as is exemplified in the drawings, the collet 90 includes four legs 93. It will be appreciated that a collet 90 having more or fewer than four but at least two legs 93 may be provided. The collet 90 is movable along the length of a coupling component 40 either by sliding along a portion, such as the proximal portion 46 that is free of texture or engagement features, or by engagement with corresponding coupling features such as one or more threads 45. According to the depicted embodiment, the legs 93 of the collet body 92 ring are adapted with interior engagement features comprising an engagement feature 97 that is complimentary to the engagement feature of the coupling component 40. In the exemplified embodiment, each of the engagement feature 97 of the collet 90 and the engagement feature 97 of the coupling component 40 comprises a thread 45. Applying rotational distally directed force to the collet 90 drives its translation distally along the coupling component 40.

Of course, as described elsewhere herein, both the collet 90 and the coupling component 40 may be devoid of any surface features, wherein retention of the assembly would rely on compressive force alone, wherein the legs 93 of the collet 90 taper inward and are splayed and under tension when passed along the coupling component 40. In other embodiments, one or more interacting surface features on either or both the collet 90 and the coupling component 40 may be provided to enhance locking. According to some embodiments, the collet 90 comprises a series of spaced circumferential ridges along at least a portion of the length of its internal face from proximal to distal, the ridges adapted for resting in one or more groove features on the surface of a coupling component 40.

It will be appreciated that in some embodiments, the number and spacing of the ridges on the inner face of the collet 90 may vary such that there are more or fewer, the ridges are narrower or wider, sharper or shallower, and are equidistant or variably spaced. In addition, in alternate embodiments, a collet 90 may comprise no surface features on its internal face, other surface features or combinations thereof to either enhance sliding between a collet 90 and a coupling component 40 or to enhance friction there between. Further, such textures and features may vary along the internal face of the collet 90 to differentially enhance surface contact with a coupling component 40. It will be appreciated by those skilled in the art that other engagement features are possible and that the disclosed engagement feature is not to be limiting.

In some embodiments, all or a portion of the interior face as well as the exterior surface of the collet 90 may be textured by surface treatment or other features such as ridges, grooves, keels, fins, thread, dimples and the like to enhance engagement with and locking between the collet 90 and the coupling component 40.

In use, the collet 90 is adapted for engagement with an element such as bone whereby at least a portion of the collet body 92 is passed into a hole within the element. The collet 90 is further adapted for retention in at least one joined element by engagement of the cutting edge 94 on one or more legs 93. In the various embodiments, the cutting edge 94 is disposed along at least a portion of the length of a leg 93 which length is defined from a legs 93 proximal end adjacent the head 91 to its distal end. As shown in the drawings, the cutting edge 94 is angled opposite the direction of travel of the complimentary threads of the collet 90 and the coupling component 40, such that when the collet 90 is driven in the distal direction into engagement with an element such as bone, the cutting edge 94 passes over the bone. And when then collet 90 is driven in a proximal direction, the cutting edge 94 contacts and interferes with the at least one element such that upon proximal translation, the cutting edge 94 cuts into the element thereby inhibiting further proximal translation. This feature enhances the retention of the compressed fixation of the joined elements of the assembly 10 by preventing back out of the collet 90 that could result from motion of the joined bones.

In some embodiments, the collet 90 may comprise a collet body 92 that is elongated and extends distally to form a sleeve that extends along at least a portion of a coupling component 40 wherein the extended collet body 92 comprises engagement features such as a thread or rings for engagement with corresponding features on a plate or other device that may be affixed to a bone. In some particular embodiments, the cutting edge 94 on a leg 93 is oriented to engage one or more of the plate, ring and bone. Accordingly, in some such embodiments, the collet 90 includes on at least one or more leg 93 a cutting edge 94 along at least a portion of the length of the leg 93 the edge oriented to cut into at least one joined element when the collet 90 is rotated to translate proximally along the coupling component 40.

Figure 19:
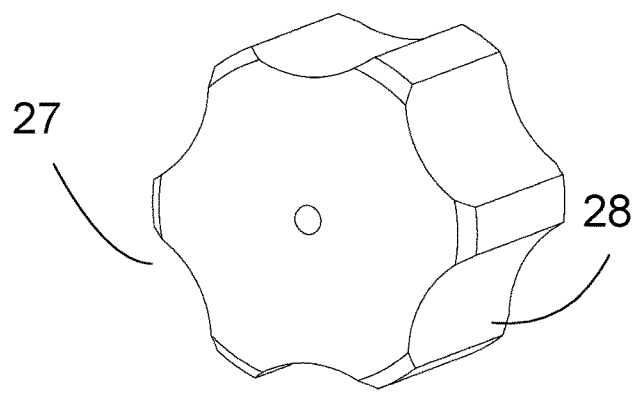
FIG. 19 shows a top perspective view of a locking knob of the tensioning locking instrument as depicted in FIG. 13 according to the disclosure.
Figure 20:
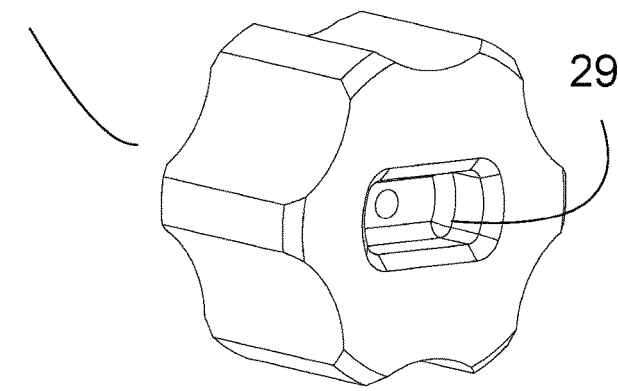
FIG. 20 shows a bottom perspective view of the locking knob as depicted in FIG. 19.
Figure 21:
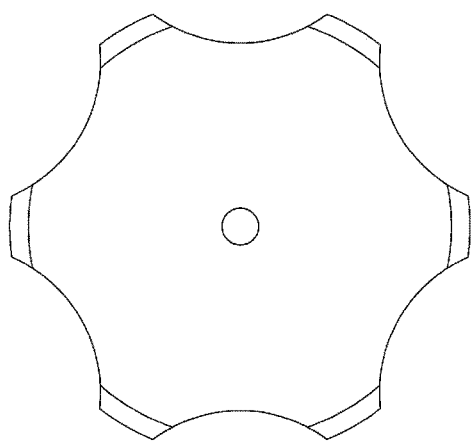
FIG. 21 shows a top view of the locking knob as depicted in FIG. 19.
Figure 22:
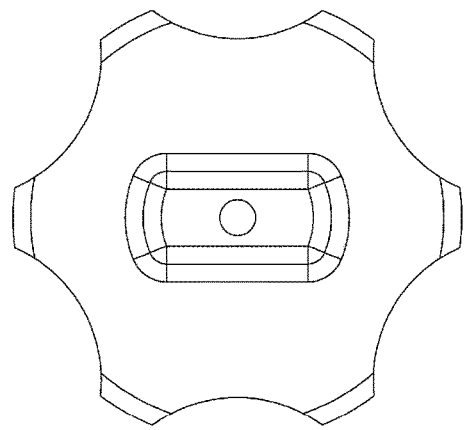
FIG. 22 shows a bottom view of the locking knob as depicted in FIG. 19.
Figure 23:
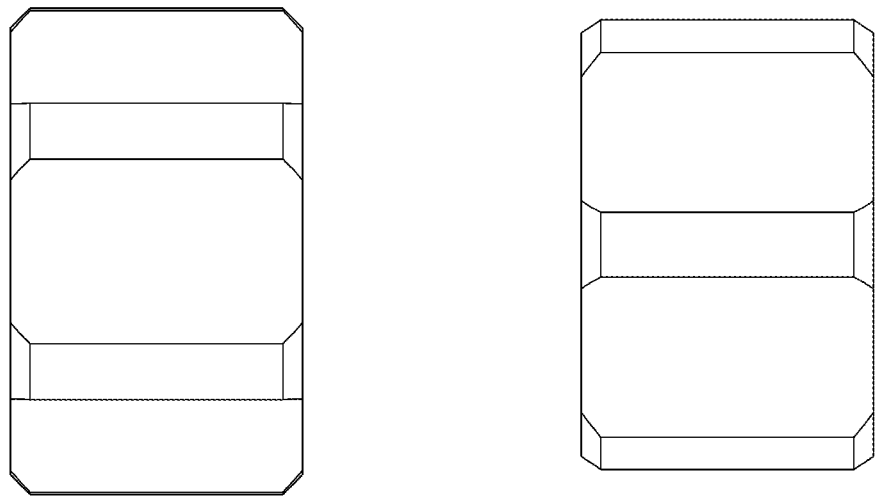
FIG. 23 shows on the left and right alternate side views of the locking knob as depicted in FIG. 19.
Figure 24:
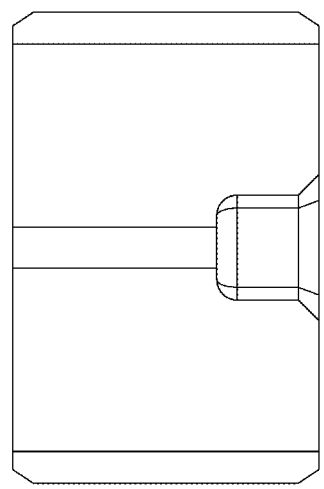
FIG. 24 shows a side view in cross section of the locking knob as depicted in FIG. 19.
Figure 29:
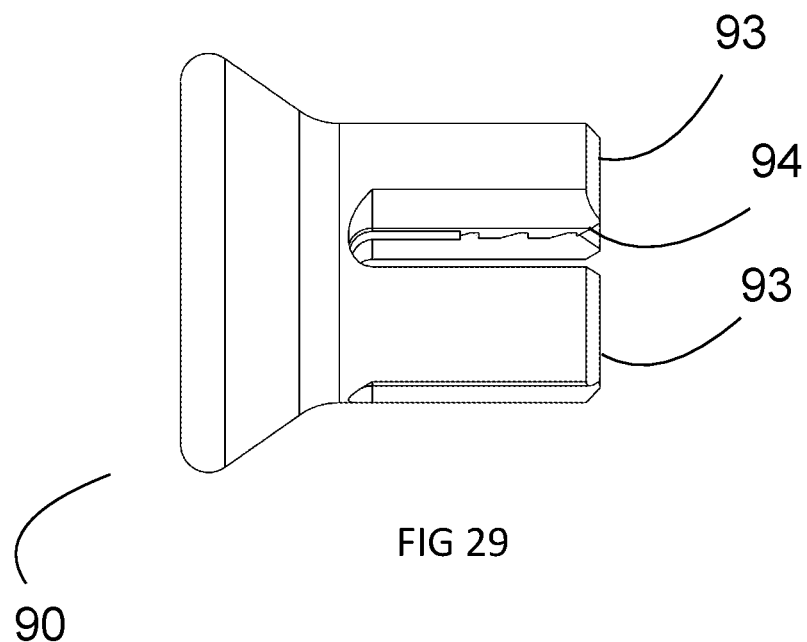
FIG. 29 shows a first side view of the locking collet as depicted in FIG. 25.
Figure 30:
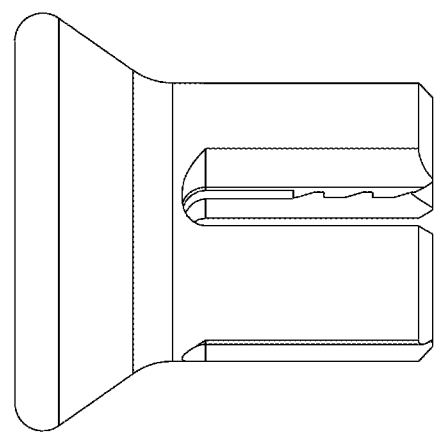
FIG. 30 shows a second side view of the locking collet as depicted in FIG. 25.
Figure 31:
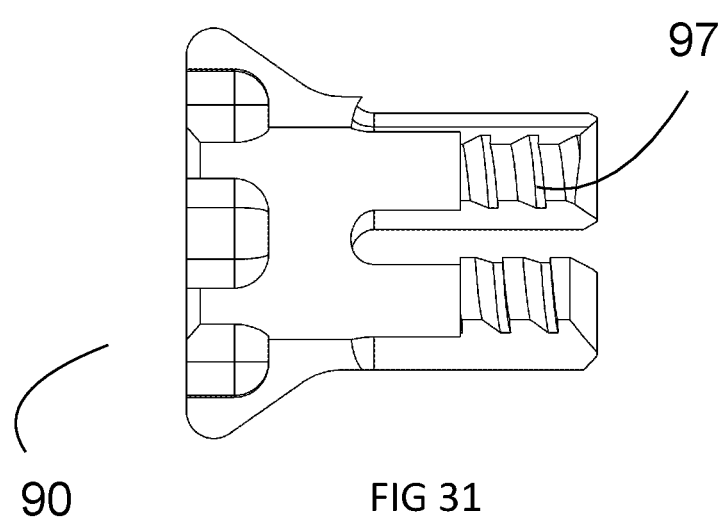
FIG. 31 shows a side view in cross section of the locking collet as depicted in FIG. 25.

Referring to the drawings, FIGS. 19 and 20 depict some such embodiments. Of course, in yet other embodiments, the distal end of the collet may extend along substantially all of the length of the coupling component 40. In some such embodiments, a further locking component (not shown) may be provided which attaches to the distal end of the coupling component 40 and extends proximally to receive and engage the distal end of the elongated collet. In some such embodiments, the extended sleeve closely contacts the surface of the coupling component 40 providing enhanced locking engagement therewith. According to such specific embodiments, the extended sleeve may be adapted with a taper to allow insertion into the proximal surface of the bone to further enhance fixation and securement to the bone. Optionally, the distal sleeve may have on its exterior surface features or texture that further enhance engagement with bone, particularly when the taper is inserted therein.

As previously described, in some embodiments, one or more adaptations to a collet 90 are contemplated to enable ready use with elements selected from orthopedic stabilization implants, such as, for example, medical textiles, and stabilization plates, such as bone plates, formed from a metal or other suitable implant material. In accordance with one such embodiment, the collet 90 is adapted to be engaged within a through channel or seat in a stabilization implant. In various embodiments, the stabilization implant comprises one or more receivers that are shaped and comprise engagement features, such as threads, for achieving locking engagement with a collet 90. In an exemplary embodiment, the seat in the stabilization implant may be cylindrical, or may be concave and frusto hemispherical or frustoconical and at least a portion of the collet body 92 or an extension thereof of the collet 90 is correspondingly shaped, and each are adapted with engagement features, and in some examples are threaded. In another exemplary embodiment, the seat in the stabilization implant is a cylindrical through channel and the collet body 92 includes a portion that is cylindrically shaped along at least at a portion of its length from its proximal end to its distal end, and each is threaded for engagement. One of ordinary skill will appreciate that the corresponding shapes and engagement features may vary. Moreover, it will also be appreciated that a stabilization implant may comprise one or more types of engagement features for collets 90 according to the instant invention, as well as for fasteners known in the art such as conventional screws. Further, it will be appreciated that stabilization implants may be provided preassembled for use with one or more collets 90 according to the instant invention.

Systems, Instruments and Methods for Engaging and Tensioning System Components

Referring again to the drawings, FIG. 7-FIG. 12 show alternate views of an embodiment of a system according to the disclosure, the system including an assembly 10 and a tensioning instrument 20. FIG. 13-FIG. 24 show alternate views of an embodiment of a tensioning instrument 20. The tensioning instrument 20 has an overall generally cylindrical shape and includes a housing 21 having a central cannula 26, the housing 21 including in some embodiments surface features and/or texturing along at least a portion of its surface to facilitate stable grasping. The tensioning instrument 20 also includes a housing handle 22, and elongate shaft 23, each of which portions may have the same or different circumferential dimensions and lengths, and each of which may or may not include surface features/texturing along at least a portion of their surfaces. The tensioning instrument 20 is defined along its length between proximal and distal ends, the distal end including an engagement means 24 for engagement with a collet 90, the proximal end including a knob 25 that actuates the driving motion of the tensioning instrument 20. As shown in the depicted embodiments, the knob 25 is generally block shaped and has a length dimension that is approximately the same as the diameter of the adjacent housing handle 22 and has a width dimension that is a fraction of the diameter of the adjacent housing handle 22. In other embodiments, the knob 25 may have a different shape. The tensioning instrument 20 includes in some embodiments a removable handle 27 that includes a handle grip 28 and a knob receiver 29 that is complementary to and engageable with the knob 25. The cannula 26 is adapted to receive the coupling component 40.

REPRESENTATIVE EMBODIMENT OF A METHOD

In one example of use, a metatarsal fracture may be fixated with an embodiment of a compression fastening system according to this disclosure, wherein an untrimmed coupling component is passed through two or more bone fragments of the metatarsal bone to be joined, the coupling component extending proximally out of an upper surface of the fractured bone, with a collet engaged with the coupling component and secured into contact with the proximal bone surface. An anchor is oriented opposite from the collet and on the distal side of the distal (lower) bone fragment, such that tensioning of the coupling component between the collet and the anchor achieve locked fixation between the bone and the collet facilitated by one or more cutting edges on the collet. In use by an operator, the coupling component 40 is passed through the cannula 26 of the tensioning instrument 20, and in embodiments wherein the toggle anchor 70 has a toggle shape, the toggle is flipped into a closed configuration to allow passage through the cannula 26. Installation of the components of the exemplary compression fixation assembly 10 for element fixation, including bone element fixation as described above, includes initial selection of a collet 90 for engagement with the coupling component 40, wherein the coupling component 40 is passed through the through channel 95 of the collet 90 prior to insertion of the coupling component 40 in the tensioning instrument 20 cannula 26. An toggle anchor 70 component of the coupling component 40 is then actuated to engage with the element that is most distant from the operator, and the selected collet 90 is slid over the coupling component 40 in a coaxial orientation towards the two or more elements and pressed against the element most proximal to the operator while the tensioning instrument 20 is actuated by rotation of the collet 90 until the desired compression is achieved. The assembly 10 is then actuated into a locked configuration between the coupling component 40, the collet 90 and the proximal element, to thereby fix the assembly and maintain the desired compression. Features of the collet 90 including one or more cutting edges 94 on collet legs 93 prevent back out of the collet 90.

When the elements being compressed are bone, then, consistent with suitable clinical practice, the system is retained intact so that compression is maintained over the clinically appropriate healing period. In some embodiments, the compression fixation system is adjusted during the healing to maintain, increase, or reduce compression. Optionally, the system may be removed from the bone after healing.

Of course, it will be appreciated that the assembly may be used with other coupling components 40 that lack a toggle anchor 70 and comprise other features that are not described herein. Indeed, in some embodiments, the assembly may be adapted and scaled to engage with coupling components 40 that are substantially smaller than bone pins and wires, and with coupling components 40 that are on a substantially larger scale. Accordingly, the references to "proximal" and "distal" in regard to the exemplary coupling components 40 described herein are not intended to be limiting, and generically, the orientation of the assembly as used herein and as may be used in other applications is not in any way limiting.

One or more components of the assembly and instruments hereof may be formed out of any suitable biocompatible material and combinations thereof, including those used conventionally in the art. Such materials include but are not limited to: metals such as, for example, stainless steel (such as 316 LVM, per ASTM F1350, electropolished and passivated), titanium alloys (such as TI-6AL-4V, per ASTM F136), cobalt alloys, superelastic metals, such as nitinol; polymers, such as polyester and polyethylene, polyether ether ketone (PEEK); and resorbable synthetic materials such as, for example, suture material and polylactic acid.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

The invention claimed is:

1. A compression fastener system comprising:
 a. a coupling component having proximal and distal ends, a central axis, and a surface comprising an engagement feature along at least a portion of a length of the coupling component,
 b. an anchor at the distal end of the coupling component,
 c. a generally cylindrical collet having proximal and distal ends and comprising a distal body that comprises two or more legs, at least one leg having a cutting edge along at least a portion of its length, and a proximal head that includes at least one tool receiver, the collet further having a through channel from the proximal to the distal end, and comprising a surface that includes an engagement feature that is complimentary to the coupling component engagement feature,
 wherein the assembly, when assembled, may be provisionally locked to enable controlled linear movement of the collet along the axis of the coupling component.

2. The compression fastener system according to claim 1, the coupling component comprising an elongate wire.

3. The compression fastener system according to claim 2, wherein the anchor is selected from a threaded shank and a toggle.

4. The compression fastener system according to claim 3, wherein the anchor is a toggle engageable with the coupling component in a cantilever pivotal arrangement, such that in one configuration, the toggle is pivoted into linear alignment with the coupling component and is nested within a recess therein, and in a second configuration, the toggle is deployed in a generally perpendicular orientation relative to the axis of the coupling component.

5. The compression fastener system according to claim 4, wherein the toggle is formed of a memory metal and has a shape that transforms to provide enhanced tension when the assembly is locked to two or more elements that are compressed between the anchor and the collet.

6. The compression fastener system according to claim 5, wherein at least one of (i) at least a portion of an outer surface of a distal end of the coupling component and (ii) at least a portion of an inner face of the collet comprises an engagement feature selected from one or a combination of ridges, grooves, keels, fins, threads, dimples, knurls, and surface texturing, and wherein the engagement features of the at least one of the outer surface of the coupling component and the inner face of the compressible collet cooperate with the opposing surface of the assembly when the assembly is in an engaged configuration to enhance the compressive securement of the locked compression fixture system.

7. The compression fastener system according to claim 6, wherein the collet comprises four legs.

8. The compression fastener system according to claim 7, wherein each leg comprises a cutting edge along at least a portion of its length from proximal to distal.

9. The compression fastener system according to claim 6, wherein the engagement features of each of the collet and the coupling component are threads, and wherein the cutting edges of the legs are oriented on a trailing edge of the legs relative to the threads such that when the collet is driven in a distal direction along the threads the cutting edges are trailing, and when the collet is driven in a proximal direction along the threads, the cutting edges are leading.

10. The compression fastener system according to claim 3, wherein the distal end of the coupling component includes a split that is parallel to the long axis of the coupling component, and wherein the anchor is a toggle engageable with a fastener within the slit in the distal end of the coupling component, such that in one configuration, the toggle is pivoted into linear alignment with the coupling component and is nested within the slit, and in a second configuration, the toggle is deployed in a generally perpendicular orientation relative to the axis of the coupling component.

11. The compression fastener system according to claim 10, wherein the toggle when oriented along the axis of the coupling component extends beyond the end of the coupling component.

12. The compression fastener system according to claim 10, wherein the toggle is radiused on at least one of two ends.

13. The compression fastener system according to claim 10, wherein the toggle is shaped on at least one of two ends, the shape selected from squared, sharpened, rounded and conical.

14. The compression fastener system according to claim 1, wherein the compression component includes along all or a portion of its length indicia to enhance visibility of the engagement feature, the indicia selected from laser deposited coloration that may be one of solid coloration, varied colors, patterning and combinations of these.

15. A compression fastener system comprising:
  a. a coupling component having proximal and distal ends, a central axis, and a surface comprising an engagement feature along at least a portion of a length of the coupling component,
  b. an anchor at the distal end of the coupling component, wherein the anchor is a toggle engageable with the coupling component in a cantilever pivotal arrangement, such that in one configuration, the toggle is pivoted into linear alignment with the coupling component and is nested within a recess therein, and in a second configuration, the toggle is deployed in a generally perpendicular orientation relative to the axis of the coupling component, and
  c. a generally cylindrical collet having proximal and distal ends and comprising a distal body that comprises two or more legs, at least one leg having a cutting edge along at least a portion of its length, and a proximal head that includes at least one tool receiver, the collet further having a through channel from the proximal to the distal end, and comprising a surface that includes an engagement feature that is complimentary to the coupling component engagement feature, wherein the cutting edges of the legs are oriented on a trailing edge of the legs relative to the threads such that when the collet is driven in a distal direction along the threads the cutting edges are trailing, and when the collet is driven in a proximal direction along the threads, the cutting edges are leading,
  wherein the assembly, when assembled, may be provisionally locked to enable controlled linear movement of the collet along the axis of the coupling component.

16. The compression fastener system according to claim 15, wherein at least one of (i) at least a portion of an outer surface of a distal end of the coupling component and (ii) at least a portion of an inner face of the collet comprises an engagement feature selected from one or a combination of ridges, grooves, keels, fins, threads, dimples, knurls, and surface texturing, and wherein the engagement features of the at least one of the outer surface of the coupling component and the inner face of the compressible collet cooperate with the opposing surface of the assembly when the assembly is in an engaged configuration to enhance the compressive securement of the locked compression fixture system.

* * * * *